United States Patent [19]

Wegner et al.

[11] Patent Number: 4,482,721

[45] Date of Patent: Nov. 13, 1984

[54] 1,2,4-TRIAZOLE-BLOCKED POLYISOCYANATES AS CROSS-LINKERS FOR LACQUER BINDERS

[75] Inventors: Christian Wegner, Cologne; Hanns-Peter Müller, Leverkusen; Hans J. Kreuder, Krefeld, all of Fed. Rep. of Germany

[73] Assignee: Bayer Aktiengesellschaft, Leverkusen, Fed. Rep. of Germany

[21] Appl. No.: 387,463

[22] Filed: Jun. 11, 1982

Related U.S. Application Data

[63] Continuation of Ser. No. 21,959, Mar. 19, 1979, abandoned.

[30] Foreign Application Priority Data

Mar. 21, 1978 [DE] Fed. Rep. of Germany ....... 2812252

[51] Int. Cl.$^3$ .......................................... C07D 249/08
[52] U.S. Cl. ...................................... 548/262; 427/27; 106/127
[58] Field of Search .......................................... 548/262

[56] References Cited

U.S. PATENT DOCUMENTS 3,248,398  4/1966  Mühlbauer et al. ................ 548/262
3,308,131  3/1967  McKusick ........................... 548/262
3,404,159  10/1968  Strobel et al. ..................... 548/262

Primary Examiner—Glennon H. Hollrah
Assistant Examiner—James H. Turnipseed
Attorney, Agent, or Firm—Connolly and Hutz

[57] ABSTRACT

1,2,4-Triazole-blocked polyisocyanates are excellent crosslinking agents for polyhydroxyl compounds. Their comparatively high melting point makes these compositions particularly suitable for coatings which are applied by fluidisation dip coating or electrostatic powder spraying.

2 Claims, No Drawings

1,2,4-TRIAZOLE-BLOCKED POLYISOCYANATES AS CROSS-LINKERS FOR LACQUER BINDERS

This application is a continuation of application Ser. No. 21,959 filed Mar. 19, 1979 and now abandoned.

This invention relates to blocked polyisocyanates and to lacquer binders, particularly powder lacquer binders, which contain these blocked polyisocyanates as cross-linkers.

The production of blocked polyisocyanates is known (cf. for example, Houben-Weyl, Methoden der organischen Chemie, Vol. XIV/2, 4th Edition, George Thieme Verlag, Stuttgart 1963, pages 61 to 70). Of the numerous blocking agents described in the literature for organic polyisocyanates, only a few have acquired any commercial significance. For solvent-containing stoving lacquers, masking with malonic acid and acetoacetic acid esters is conventional (for example German Pat. No. 756,058), while powder lacquer cross-linkers as used in conventional processes are generally blocked with lactams or phenols (for example German Auslegeschrift No. 1,957,483 and East German Pat. No. 55,820).

Unfortunately, none of these compounds ideally satisfies the requirements imposed on masking agents. Although, in the case of malonic and acetoacetic esters, the deblocking temperature is low (e.g. from 120° to 130° C./30 minutes), these substances have to be used in large quantities by weight on account of the relatively high molecular weight thereof or, in other words, the proportion by weight of the masked NCO-groups is distinctly reduced. In addition, systems of this type often have no resistance to yellowing on stoving. The use of phenols as blocking agents is limited on account of the physiological properties of these compounds and the obnoxious odour thereof, while in cases where $\epsilon$-caprolactam is used as blocking agent high stoving temperatures (at least 160° C./30 minutes) have to be applied to obtain complete cross-linking.

One of the characteristics of electrostatic powder spraying is that thicker layers are formed in some places (e.g. on horizontal surfaces, in corners and angles) than on the rest of the substrate. However, when the layer thickness exceeds a certain limit (generally from 120 to 150 m$\mu$), surface faults are readily developed in these places during the stoving process. Accordingly, it frequently happens that the lacquer finish of an article excellently coated as a whole is locally spoiled, generally by bubble formation.

It has now surprisingly been found that the properties of conventional powder lacquer binders may be even further improved by using as cross-linkers compounds containing from 2 to 4 1,2,4-triazole-blocked isocyanate groups which preferably have a melting point of from 50° to 220° C. and an average molecular weight of from 306 to 1000.

In addition, it has been found that these binders are also eminently suitable for the production of solvent-containing stoving lacquers.

U.S. Pat. No. 3,248,398 describes the blocking of monoisocyanates with heterocyclic compounds containing H-N-groups, the blocked monoisocyanates being recommended for the impregnation of textiles and paper. The long list of heterocyclic compounds mentioned also includes 1,2,4-triazole. However, there is nothing in this reference to suggest that polyisocyanates blocked with this particular triazole have certain properties by virtue of which they may be used in particular as cross-linkers for polyurethane powder lacquers.

According to U.S. Pat. No. 3,721,645, prepolymers containing NCO-groups which have been reacted with triazoles, for example 1,2,4-triazole, may be used as coating agents, injection-moulding resins, PVC additives, rotational moulding resins and fluidisation dip coating powders (column 3, lines 63 to 67; column 4, line 3). They have the advantage of melting at relatively high temperatures and hardening at relatively low temperatures (column 4, lines 5 to 9, 30 to 35). Reactive hydrogen-containing compounds having a molecular weight of at least 1000 are said to be particularly suitable starting compounds (column 3, lines 59 to 63). The polyisocyanate, the reactive hydrogen containing compound and the triazole may be reacted by the prepolymer method or by the one-pot process (column 2, lines 38 to 44).

If the products according to U.S. Pat. No. 3,721,645 are to be used as powder lacquer binders, levelling difficulties may be expected to occur during stoving on account of the relatively high molecular weight and the resulting high melt viscosity of the compounds in question.

Accordingly, the present invention relates to compounds containing from 2 to 4 1,2,4-triazole-blocked isocyanate-groups, preferably having a melting point of from 50° to 220° C., more particularly from 70° to 200° C., characterised in that they have an average molecular weight of from 306 to 1000.

The average molecular weight is determined by vapour pressure osmometry using acetone as solvent.

The present invention also relates to lacquer binders, particularly powder lacquer binders, based on polyhydroxyl compounds, these lacquer binders containing the 1,2,4-triazole-blocked compounds as cross-linkers.

The polyisocyanates known from polyurethane chemistry may be used as starting materials for producing the blocked polyisocyanates according to the present invention. These known polyisocyanates generally contain from 2 to 4 isocyanate groups and have a molecular weight of from 168 to 850. The polyisocyanates in question are either simple polyisocyanates, such as hexamethylene diisocyanate, 2,4-diisocyanato toluene, 2,6-diisocyanato toluene, 1-isocyanato-3,3,5-trimethyl-5-isocyanatomethyl cyclohexane (=isophorone diisocyanate=IPDI), 4,4'-diisocyanatodiphenyl methane, 2,4'-diisocyanato diphenyl methane, or derivatives of these diisocyanates containing biuret or urethane groups. The derivatives containing biuret groups which are of particular interest in this respect include particularly polyisocyanates of the type described in U.S. Pat. No. 3,124,605, i.e. mixtues of homologues consisting of tris-(isocyanatohexyl)-biuret and higher homologues of this polyisocyanate, of the type obtained in the biuretisation of hexamethylene diisocyanate. These biuret polyisocyanates also have an average NCO-functionality of from 3 to 4 and an average molecular weight below 850. Suitable urethane derivatives of the diisocyanates exemplified above include in particular their reaction products with less than equivalent quantities of aliphatic diols or triols having molecular weights of from 62 to 200, such as ethylene glycol, 1,2- or 1,3-propane diol, 1,2-butane diol, tetramethylene or hexamethylene glycol, diethylene glycol, trimethylol propane or glycerol. In the production of these urethane-modified derivatives of the above-mentioned diisocyanates, the diisocyanates are reacted with the exemplified polyhydric alcohols in quantitative ratios which correspond to an NCO/OH-equivalent ratio of at least 2:1, preferably from 2:1 to 20:1. The urethane-modified polyisocyanates obtainable in this way also have NCO-functionalities of from 2 to 4, preferably from 2 to 3, and (average) molecular weights below 850.

The reagent used for blocking the exemplified polyisocyanates in accordance with the present invention is the blocking agent essential according to the present invention, 1,2,4-triazole. The blocking agent essential according to the present invention is preferably used as the sole blocking agent. However, it may also be used in conjunction with other known blocking agents, such as ε-caprolactam or phenols.

The reaction of the starting polyisocyanates with the blocking agent may be carried out in the presence of aprotic solvents which are inert to isocyanate groups, or in the melt. Suitable solvents are, for example, ethyl acetate, butyl acetate, acetone, methylethyl ketone, methylisobutyl ketone, tetrahydrofuran or dioxane. Thwe blocking reaction is generally carried out at temperatures of from 40° to 160° C., preferably from 60° to 130° C. At reaction temperatures above 60° C., the reaction may be carried out in the absence of catalysts and, in most cases, is over after only from 30 to 60 minutes. The blocking agent is preferably used in an at least equivalent quantity. In many cases, it is advisable to use a slight excess in order to obtain complete masking. In the case of the above-mentioned, but by no means preferred, simultaneous use of other blocking agents, the 1,2,4-triazole is always used in such quantities that the blocked polyisocyanates according to the present invention contain at least two 1,2,4-triazole-blocked isocyanate groups per molecule.

In cases where the exemplified urethane-modified polyisocyanates are used as starting material, the production and blocking thereof may be carried out in a single-stage reaction in which the non-urethane-modified diisocyanate is reacted with a mixture of blocking agent and one or more of the exemplified polyols. The foregoing comments regarding the quantitative ratios between the reactants also apply to this embodiment of the production of the blocked polyisocyanates according to the present invention, the comments on the ratio between NCO-groups and NH-groups naturally applying only to those NCO-groups which are not required for the reaction with the hydroxyl groups.

In the production of the products according to the present invention, the blocking agent may be initially introduced and the polyisocyanate to be blocked subsequently added thereto, or vice versa, i.e. the blocking agent may be added to the starting isocyanate, optionally together with the alcohol used to modify the starting isocyanate. Where a mixture of polyol and triazole is used for producing the compounds according to the present invention, it is particularly advantageous to convert this mixture, by heating, into a clear melt which is then added to the isocyanate by means of a steam-heated dropping funnel.

In cases where the compounds according to the present invention are produced in the presence of a solvent for the starting materials, the blocked polyisocyanates often crystallise out and may be recovered as a solid by simple filtration.

In general, compounds according to the present invention produced from specific starting materials have a clearly defined molecular weight and a precise melting point. In cases where polyisocyanate mixtures and-/or mixtures of different blocking agents are used and particularly in cases where the exemplified biuret- or urethane-modified starting isocyanates are used for producing the blocked polyisocyanates according to the present invention, the blocked polyisocyanates are mixtures of different compounds having the average molecular weight specified above.

The blocked polyisocyanates according to the present invention are valuable cross-linkers for polyhydroxyl compounds and may be used, particularly in combination with polyhydroxyl compounds having a softening point above 50° C., preferably from 60 to 120° C., as heat-cross-linkable two-component binders for powder lacquers. In this respect, the use of the blocked polyisocyanates according to the present invention affords the following particular advantages:

1. By virtue of the low molecular weight of the 1,2,4-triazole, only relatively small quantities of the blocking agent are required for blocking the isocyanate groups, so that the proportion by weight of the blocking agent eliminated during cross-linking remains relatively low.
2. The blocking agent essential according to the present invention is physiologically far more acceptable than other conventional blocking agents.
3. The comparatively high melting point of the blocked polyisocyanates according to the present invention makes them particularly suitable for coatings which are applied by fluidisation dip coating or by electrostatic powder spraying (EPS) and subsequently subjected to heat treatment. This, where isophorone diisocyanate, for example, is used as the isocyanate component, there is no need to modify it, as described, for example, in German Auslegeschrift No. 2,215,080, with loss of about half the isocyanate groups, instead it is sufficient to extend only about 15% of the isocyanate grous in the IPDI by polyhydric alcohols in order to guarantee adequate fluidity of the powders.
4. Another advantage is the comparatively low stoving temperature (approximately 150° C.) of the powder lacquers containing polyisocyanates blocked in accordance with the present invention as cross-linkers. The blocked polyisocyanates according to the present invention are generally used in such quantities that from 0.8 to 1.2, preferably about 1, blocked isocyanate group of the blocked polyisocyanates according to the present invention is available per isocyanate-reactive group of the binder.

In addition, the type of blocked polyisocyanates according to the present invention and/or the type of component containing isocyanate-reactive groups used in accordance with the present invention is/are selected in such a way that the binder in the form in which it is ready for use has a melting point above 40° C., preferably from 40° to 100° C., i.e. melts at temperatures within this range to form a film-forming liquid.

Reactants for the blocked polyisocyanates according to the present invention as used in accordance with the present invention are, in particular, organic polyhydroxyl compounds having the above-mentioned melting or softening point. It is preferred to use relatively high molecular weight polyhydroxyl compounds having hydroxyl numbers of from 40 to 250, preferably from 40 to 150. Examples of such compounds include: polyesters containing hydroxyl groups, polyethers containing hydroxyl groups, polyurethanes containing hydroxyl groups, polyester urethanes containing hydroxyl groups, urethane-alkyl resins containing hydroxyl groups, acrylic resins containing hydroxyl groups, epoxide resins containing hydroxyl groups and mixtures thereof. Polyester polyols are preferred. These polyester polyols may be obtained by known methods, preferably from cyclic polycarboxylic acids, such as phathalic acid, isophthalic acid, terephthalic acid, benzene-1,2,4-tricarboxylic acid, 3,6-dichlorophthalic acid, tetrachlorophthalic acid, tetrahydrophthalic acid, hexahydrophthalic acid, endomethylene tetrahydrophthalic acid and, where obtainable, the anhydrides or $C_1$–$C_4$ alkyl esters thereof and trimellitic acid anhydride, also diols such as ethylene glycol, 1,2-1,3-propane diol, 1,2- or 1,4-butane diol, 2,2-dimethylpropane diol, 2,5- or 1,6-hexane diol, 4,4'-dihydroxy dicyclohexyl-2,2-propane, cyclohexane diol, dimethylol cyclohexane, diethylene glycol and 2,2-bis-[4-($\beta$-hydroxyethoxy)-phenyl]-propane and polyols, such as glycerol, hexane triol, pentaerythritol, sorbitol, trimethylol ethane or propane and tris-($\beta$-hydroxyethyl)-isocyanurate.

Monocarboxylic acids, for example benzoic acid, t-butyl benzoic acid, hexahydrobenzoic acid, saturated and/or unsaturated fatty acids and acyclicpolycarboxylic acids, such as adipic acid, maleic acid and succinic acid, may be co-condensed in small quantities.

It is also possible, although less preferred, to use polyvinyl and polyvinylidene resins having hydroxyl numbers in the above-mentioned range, of the type which may be obtained in known manner by copolymerising suitable monomers, such as hydroxypropyl-(meth)-acrylic acid ester, hydroxyethyl-(meth)-acrylic acid ester, ethyl acrylate, butyl acrylate, 2-ethylhexyl acrylate, methyl methacrylate, ethyl methacrylate, butyl methacrylate, lauryl methacrylate, styrene, $\alpha$-methyl styrene, vinyl toluene, acrylonitrile, acrylamide, vinyl acetate, acrylic acid and methacrylic acid, in the presence of initiators and regulators.

It is also possible, although less preferred, to use known polyether polyols providing they satisfy the above-mentioned requirements with regard to melting or softening point.

Polyepoxide resins, for example reaction products of bisphenol A with epochlorhydrin, may also be used in the powder lacquer binders.

Conventional additives, such as pigments, levelling agents, fillers and catalysts, of the type mentioned, for example, in German Pat. No. 946,173, may also be added.

The films are produced in the conventional way. Both components and any auxiliaries are thoroughly mixed, for example in an edge-runner mixer, and the resulting mixture subsequently homogenised in an extruder at from 90° to 120° C. After cooling, the material is ground to a particle size of less than 100 $\mu$m, the powder is applied to the substrate in a powder spraying machine and subsequently stoved.

In addition to good surface properties, the films hardened using 1,2,4-triazole-masked isocyanates show extemely high resistance to solvents, elasticity, yellowing resistance and weather resistance. The percentages given below are percentages by weight.

EXAMPLE 1

Production of a 1,2,4-triazole-blocked isocyanate 73 g of 1,2,4-triazole are added in portions at 25° C. to 84 g of hexamethylene diisocyanate dissolved in 750 ml of ethyl acetate. After half the triazole had been added, a deposit begins to precipitate. After all the 1,2,4-triazole has been added, the mixture is boiled under reflux for 30 minutes. After cooling, the reaction product obtained in a quantitative yield is filtered off. Melting point: 175° C.

EXAMPLE 2

Production of a 1,2,4-triazole-blocked isocyanate 52 g of 2,4- tolylene diisocyanate in 1000 ml of acetone are introduced into a nitrogen-purged flask. 44 g of 1,2,4-triazole are added in portions with stirring at room temperature. After half the 1,2,4-triazole has been added, a deposit begins to precipitate. After the triazole has been added, the mixture is boiled under reflux for 30 minutes. After cooling, the reaction product obtained in a quantitative yield is filtered off. Melting point: 206° C.

EXAMPLE 3

Production of a 1,2,4-triazole-blocked isocyanate 250 g of 4,4'-diisocyanatodiphenyl methane are dissolved in 3000 ml of ethyl acetate at 60° C. 145 g of 1,2,4-triazole are added in portions. After boiling under reflux for 1 hour and cooling, the deposit is filtered off under suction. Yield: 372.2 g, m.p.: 212° C., NCO (masked): 21.3%.

EXAMPLE 4

Production of a 1,2,4-triazole-blocked biuret- modified isocyanate 151 g of 1,2,4-triazole are added in portions, with stirring, at 100° C., to 400 g of biuret polyisocyanate, produced by biuretising hexamethylene diisocyanate in known manner, having an NCO-content of 21.9%, by weight, at such a rate that the temperature does not exceed 120° C. After stirring for 3 hours, no more free isocyanate is present. The mass solidifies at room temperature to form a clear, pale yellow tough resin. NCO (masked): 15.9%; average functionality: 3.

EXAMPLE 5

Production of a 1,2,4-triazole-blocked urethane-modified isocyanate 840 g of hexamethylene diisocyanate and 45 g of 1,4-butane diol are stirred for 1 hour at 90° C. The solution is then freed from the excess hexamethylene diisocyanate at 155° C./0.2 Torr in a thin layer evaporator. A white, wax-like mass is obtained after cooling. NCO: 20.3% (theoretical value 19.7%).

158 g of 1,2,4-triazole are added in portions, at 100° C., to 450 g of the modified diisocyanate at such a rate that the temperature rises to 130° C. When no more free isocyanate may be detected, the mixture is cast onto a metal plate on which it solidifies into a white mass. Melting point: 118° C., NCO (masked): 15.0%.

EXAMPLE 6

Production of a 1,2,4-triazole-blocked urethane-modified isocyanate

A melt of 90 g of 1,4-butane diol and 148 g of 1,2,4-triazole is added to 336 g of hexamethylene diisocyanate heated to 80° C. from a steam-heated dropping funnel at such a rate that, on completion of the addition, the temperature has reached 135° C. After stirring for 5 minutes at that temperature, the clear melt is then cast and immediately solidifies to form a white, brittle mass. Melting point: 128° C., NCO (masked): 14.6%.

EXAMPLE 7

Production of a 1,2,4-triazole-blocked isocyanate 580 g of 1,2,4-triazole are added in portions, at 100° C., to 888 g of isophorone diisocyanate. After stirring for 3 hours at 100° C., the melt is cast and, on cooling, solidifies into a clear brittle mass. M.p.: 74° C., NCO (masked): 22.9%.

EXAMPLE 8

Production of a 1,2,4-triazole-blocked urethane-modified isocyanate 888 g of isophorone diisocyanate and 44.2 g of trimethylol propane are stirred for 1 hour at 90° C. 510 g of 1,2,4-triazole are then added in portions at such a rate that the temperature does not rise above 120° C. After 3 hours, no more free isocyanate may be detected. The clear colourless melt is cast and, on cooling, solidifies into a clear, brittle mass. Melting point: 78° C., NCO (masked): 20.3%.

EXAMPLE 9

Production of a 1,2,4-triazole-masked solvent-containing isocyanate 666 g of isophorone diisocyanate and 600 g of ethyl glycol acetate are introduced into a flask equipped with a stirrer, internal thermometer and reflux condenser. Following the addition of 67 g of trimethylol propane and 42 g of ethane diol, the mixture is stirred for 1 hour at 90° C. 215 g of 1,2,4-triazole are then added in portions, followed by stirring for 3 hours. A clear, colourless storable solution is obtained. Solids content: 62%, NCO (masked): 8.1%.

EXAMPLE 10

Production of a coating from the solvent phase 145 g of the blocked solvent-containing isocyanate described in Example 9 are mixed with 100 g of a polyacrylate having an OH-group content of 4.8% and the resulting mixture is applied to a metal plate which is heated to 120° C. for 30 minutes. An elastic, solvent-resistant clear coating is obtained.

EXAMPLE 11

Production of a coating from the solvent phase 81 g of the blocked isocyanate produced in accordance with Example 14 are mixed with 100 g of a polyester solution (65% in xylene/ethyl glycol acetate, OH=5.2%, acid number<4) while heating. The mixture is then applied to an iron plate and stoved for 30 minutes at 130° C. A clear, acetone-resistant elastic film is obtained.

EXAMPLE 12

Production of a coating by electrostatic powder spraying 50.5 parts of a polyester produced from terephthalic acid, neopentyl glycol and trimethylol propane (OH-number 50, melting point: 65° C., acid number:<10) are homogenised for from 30 to 60 seconds at from 100° to 120° C. in an extruder with 9.0 parts of the 1,2,4-triazole-masked isocyanate produced in accordance with Example 8, 29.9 parts of titanium white pigment (rutile) and 0.6 part of a conventional commercial-grade levelling agent, followed by grinding in a mill to a particle size of <100μ. The powder is applied to degreased iron plates by the EPS process (voltage 60 kV) and stoved. Solvent-resistant, elastic and light-stable coatings having the following characteristics are obtained:

| Stoving conditions | [mins./°C.] | 30/140 | 30/160 | 7/200 |
|---|---|---|---|---|
| Thickness | [μ] | 62–74 | 60–65 | 49–58 |
| Glass DIN 67 530 | [according to Gardner 60° C.] | 89 | 88 | 88 |
| Lattice cut DIN 53 151 | | 0 | 0 | 0 |
| Reverse impact | [inch × lbs] | >100 | >100 | >100 |
| Erichsen indentation DIN 53 156 | [mm] | 8 | 8 | 8 |

EXAMPLE 13

Production of a coating by electrostatic powder spraying 47.3 parts of the polyester described in Example 12 12.2 parts of the 1,2,4-triazole-masked isocyanate produced in accordance with Example 6, 39.9 parts of titanium white pigment (rutile) and 0.6 part of a conventional commercial-grade levelling agent are applied in the same way as described in Example 12. Solvent-resistant, elastic and light-stable films having the following characteristics are obtained:

| Stoving conditions | [mins./°C.] | 30/150 | 30/160 | 15/180 |
|---|---|---|---|---|
| Thickness | [μ] | 62–64 | 52–54 | 58–61 |
| Glass DIN 67 530 | [according to Gardner 60° C.] | 92 | 98 | 93 |
| Lattice cut DIN 53 151 | | 0 | 0 | 0 |
| Reverse impact | [inch × lbs] | >100 | >100 | >100 |
| Erichsen indentation DIN 53 156 | [mm] | >10 | >10 | >10 |

We claim:

1. A compound having an average molecular weight of from 306 to 1,000 and a melting point of from 50° to 220° C., said compound being selected from the group consisting of
   (a) 1,2,4-triazole-blocked isophorone diisocyanate and (b) reaction products having from two to four 1,2,4-triazole blocked isocyanate groups, said reaction products being obtained by reacting isophorone diisocyanate, 1,2,4-triazole and an aliphatic diol or triol having a molecular weight of 62 to 200.

2. A compound of claim 1 having a melting point of from 70° to 200° C.

* * * * *